United States Patent
Rathjen (10) Patent No.: US 8,136,945 B2
(45) Date of Patent: *Mar. 20, 2012

(54) OPHTHALMOLOGICAL MEASURING APPARATUS

(75) Inventor: Christian Rathjen, Bremen (DE)

(73) Assignee: SIS AG Surgical Instrument Systems (CH)

( * ) Notice: Subject to any disclaimer, the term of this patent is extended or adjusted under 35 U.S.C. 154(b) by 202 days.

This patent is subject to a terminal disclaimer.

(21) Appl. No.: 12/412,167

(22) Filed: Mar. 26, 2009

(65) Prior Publication Data

US 2009/0257025 A1    Oct. 15, 2009

Related U.S. Application Data

(63) Continuation of application No. 11/704,342, filed on Feb. 9, 2007, now Pat. No. 7,527,380.

(60) Provisional application No. 60/771,460, filed on Feb. 9, 2006.

(51) Int. Cl.
    *A61B 3/10* (2006.01)
(52) U.S. Cl. .................. 351/211; 351/205; 351/221
(58) Field of Classification Search .......... 351/205–206, 351/210–211, 221

See application file for complete search history.

(56) References Cited

U.S. PATENT DOCUMENTS

| | | | |
|---|---|---|---|
| 5,404,884 | A | 4/1995 | Lempert |
| 5,512,965 | A | 4/1996 | Snook |
| 2002/0163623 | A1 | 11/2002 | Hirohara et al. |
| 2003/0038921 | A1 | 2/2003 | Neal et al. |
| 2004/0119943 | A1 | 6/2004 | Rathjen |
| 2005/0122474 | A1 | 6/2005 | Koretz |
| 2006/0209256 | A1 | 9/2006 | Beyerlein et al. |
| 2008/0018855 | A1* | 1/2008 | Larichev et al. .............. 351/211 |

FOREIGN PATENT DOCUMENTS

| | | |
|---|---|---|
| EP | 1 430 829 | 6/2004 |
| WO | WO 01/28410 | 4/2001 |
| WO | WO 2005/027741 | 3/2005 |

OTHER PUBLICATIONS

Rozema et al., "Clinical comparison of 6 aberrometers. Part 1: Technical Specifications," J. Cataract Refract Surg, vol. 31, pp. 1114-1127, Jun. 2005.

* cited by examiner

*Primary Examiner* — Dawayne A Pinkney
(74) *Attorney, Agent, or Firm* — Ostrolenk Faber LLP (57) ABSTRACT

An opthalmological measurement apparatus (1) is proposed which comprises a first measurement system and a second measurement system. The first measurement system comprises a first light projection system for projection of a first light beam (2) through a cross-sectional part (4) of an eye (3). In addition, the first measurement system comprises image detection means, arranged in the Scheimpflug configuration with respect to the first light beam (2), for detection and storage of a cross-sectional image (30A) of at least one subregion of the cross-sectional part (4) which is illuminated by the first light projection system, from a first position outside the first light beam (2). The second measurement system comprises a second light projection system for projection of a second light beam onto the eye (3), and comprises a wavefront detector (19) for determination and storage of a wavefront profile of the second light beam reflected by the eye (3). The second measurement system allows the detection of extended measurement data which, in addition to cross-sectional images, also includes the wavefront profile, so that not only geometric eye parameters but also optical characteristics of the eye, in particular optical characteristics of the eye lens, can be determined on the basis of the detected measurement data.

16 Claims, 8 Drawing Sheets

OPHTHALMOLOGICAL MEASURING APPARATUS

CROSS REFERENCE TO RELATED APPLICATIONS

The present application is a continuation of U.S. patent application Ser. No. 11/704,342, filed Feb. 9, 2007, which claims benefit of and priority to U.S. Provisional Patent Application No. 60/771,460 filed Feb. 9, 2006, the entire contents each of which are hereby incorporated by reference.

TECHNICAL FIELD

The present invention relates to an opthalmological measurement apparatus having a measurement system. The present invention relates in particular to an opthalmological measurement apparatus having a measurement system which has a light projection system for projection of a light beam through a cross-sectional part of an eye, as well as having image detection means which are arranged in the Scheimpflug configuration with respect to the light beam, for detection and storage of a cross-sectional image of at least one subregion of the cross-sectional part illuminated by the light projection system.

PRIOR ART

Opthalmological measurement apparatuses and opthalmological measurement methods are known in the prior art in which a light projector is used to project a beam through a cross-sectional part of an eye, in particular through a cross-sectional part of the cornea. The beam is typically projected in the form of a light slit. U.S. Pat. No. 5,404,884 discloses a method and an apparatus for the investigation of corneal tissue of a patient. According to U.S. Pat. No. 5,404,884, an essentially planar laser beam with a profile in the form of a slit is projected through a cross-sectional part of the cornea. According to U.S. Pat. No. 5,404,884, a cross-sectional image of the cornea is obtained by detection of at least a portion of the light that is scattered in the cornea, that is to say of at least a portion of the light slit. According to U.S. Pat. No. 5,404,884, nebulae, the corneal thickness and the cornea topography, covering the entire cornea, are determined from a plurality of such cross-sectional images of the cornea. Since the eyes can move relative to the measurement apparatus, examination of the entire eye on the basis on the basis of U.S. Pat. No. 5,404,884 can lead to inaccuracies because these relative movements are not detected and taken into account, and because the difficulty in mutual alignment can result in measurement artifacts occurring during collation of the cross-sectional images.

EP 1430829 discloses an opthalmological measurement apparatus which uses a light projector to project a beam (for example a light slit) through a cross-sectional part of the cornea of an eye. In addition to the cross-sectional image of the illuminated cross-sectional part detected in the Scheimpflug configuration, the apparatus according to EP 1430829 also detects a view image of the eye which includes an image of the illuminated cross-sectional part. The apparatus uses the view image as the basis for determination of the relative position of the stored cross-sectional image with respect to the eye, and thus allows cohesive examination of the entire eye (for example a topography of the cornea), in which relative movements of the eye with respect to the apparatus are taken into account.

The apparatus according to EP 1430829 allows detection of measurement data for determination of geometric eye parameters such as cornea topography or cornea thickness. The measurement system according to EP 1430829 does not, however, provide sufficient data for the determination of optical characteristics of the eye, in particular of optical characteristics of the eye lens.

DESCRIPTION OF THE INVENTION

One object of the present invention is to propose an opthalmological measurement apparatus which has a light projection system for projection of a light beam through a cross-sectional part of the eye, and has image detection means arranged in the Scheimpflug configuration for detection and storage of a cross-sectional image of the illuminated cross-sectional part, which does not have the disadvantages of the known opthalmological measurement apparatuses. One particular object of the present invention is to propose an opthalmological measurement apparatus which makes it possible to detect measurement data for determination of optical characteristics of the eye, in particular of optical characteristics of the eye lens.

According to the proposed invention, these aims are achieved in particular by the elements of the independent claims. Further advantageous embodiments are also specified in the dependent claims and in the description.

The opthalmological measurement apparatus has a first measurement system which has a first light projection system for projection of a first light beam, for example in the form of a light slit, through a cross-sectional part of the eye, and image detection means, arranged in the Scheimpflug configuration with respect to the first light beam, for detection and storage of a cross-sectional image of at least one subregion of a cross-sectional part illuminated by the first light projection system, from a first position outside the first light beam.

The aims mentioned above are achieved by the present invention in particular in that the opthalmological measurement apparatus has a second measurement system, which has a second light projection system for projection of a second light beam onto the eye, and a wavefront detector for determination and storage of a wavefront profile of the second light beam reflected by the eye. In different embodiment variants, the first light projection system and the second light projection system have a common light source or their own light sources, preferably at different wavelengths. The second measurement system allows the detection of expanded measurement data which, in addition to the cross-sectional images, also includes the wavefront profile, so that not only geometric eye parameters but also optical characteristics of the eye, in particular optical characteristics of the eye lens, can be determined on the basis of the detected measurement data. The cross-sectional images of illuminated cross-sectional parts detected using the Scheimpflug configuration can be used to geometrically detect eye structures such as the eye cornea and the eye lens. The wave aberration and refractive power of the eye can be determined by detection of the wavefront profile of the light beam reflected by the eye. The combination of the two systems allows determination of an improved eye model in which, in particular, the geometry (topography) and optical characteristics of the eye lens (refractive power) are defined more accurately. In particular, the determination of the geometry of the eye lens, which is adversely affected by the slightly distorted detected cross-sectional images when using the Scheimpflug configuration, can be improved by the additional information obtained from the wavefront profile. More accurate determination of the geometry of the eye lens is particularly advantageous for the choice of intra-ocular lenses for cataracts (gray star). Nebulae in the eye lens can also be determined as a further optical characteristic of the eye lens in the cross-sectional image.

The first light projection system and the second light projection system are preferably arranged such that the first light beam and the second light beam are projected along a common radiation axis onto the eye. The radiation axis is preferably the sagittal axis or, in one alternative, the visual (or optical) axis of the eye.

The first measurement system is preferably configured to project the first light beam through a plurality of differently positioned cross-sectional parts of the eye, and to detect and to store a plurality of cross-sectional images of in each case at least one subregion of these illuminated cross-sectional parts using the Scheimpflug configuration. The measurement apparatus has, in particular, a drive module for rotation of the first measurement system essentially above a normal to the surface of the eye facing the first light projection system, or for linear movement of the first measurement system essentially at right angles to this normal. The normal preferably coincides with the sagittal axis of the eye or, in an alternative, with the visual (optical) axis of the eye. The drive module allows an automated cohesive examination of the entire eye, on the basis of a plurality of cross-sectional images. By way of example, the measurement apparatus has a processing means, which is configured to determine a cornea topography of the eye on the basis of the cross-sectional images.

In one embodiment variant, the measurement apparatus has a third measurement system which has a shielding body with a visible pattern with the shielding body being arranged such that the visible pattern is located, during application of the measurement apparatus, on a side of the shielding body facing the eye. Furthermore, the third measurement system has image detection means for detection and storage of a mirror image of the pattern on the eye. The shielding body is preferably configured and arranged such that the first light beam can be projected without any impediment through the cross-sectional part of the eye, such that the cross-sectional image can be detected without any impediment, such that the second light beam can be projected without any impediment onto the eye and such that the second light beam reflected by the eye can be detected without any impediment. The third measurement system allows the detection of extended measurement data, which includes the detected mirror image of the pattern in addition to the cross-sectional images and the wavefront profile.

In one embodiment variant, the measurement apparatus has processing means which are configured to determine a pattern-based cornea topography of the eye on the basis of the mirror image, to determine a cross-section-based cornea topography of the eye on the basis of the cross-sectional images, and to determine a combined cornea topography of the eye on the basis of the pattern-based cornea topography and of the cross-section-based cornea topography. The cross-sectional images and the detected mirror image of the pattern are thus used in a complementary manner to one another for the determination of the topography of the cornea, for example as compensation for measurement data which is incomplete as a result of the presence of eyelashes or other shadows. At this point, it should be mentioned that the expression topography in the present text is used to mean both the three-dimensional profile and the inclination profile of eye structures such as the cornea, lens etc.

The measurement apparatus preferably has a control module which is configured for selective activation of at least one of the first measurement system, the second measurement system and the third measurement system for detection of at least one of the wavefront profiles, the cross-sectional image and the mirror image. By way of example, the control module is configured to activate one or more of the measurement systems in accordance with a user-selected operating mode, in order to detect the wavefront profile, the mirror image and/or the cross-sectional image or images. Furthermore, the measurement apparatus has processing means, which are configured to determine at least one eye characteristic, corresponding to the user-selected operating mode, on the basis of the wavefront profile, the mirror image and/or the cross-sectional image or images. The selective activation allows the functionality of the measurement apparatus to be flexibly matched to the current user requirements, and the measurement systems can be activated individually or in a combined form for detection of the various measurement data items. The required measurement systems can be activated automatically, and the measurement data recorded in this way can be evaluated automatically by the processing means on the basis of the definition and configuration of the various operating modes, for example for different measurement variables and/or measurement methods.

In one embodiment variant, the control module is configured to activate a plurality of the measurement systems, corresponding to the user-selected operating mode in a defined sequence successively for detection of the wavefront profile, the mirror image and/or the cross-sectional image or images. However, the measurement data is preferably recorded simultaneously by the measurement systems.

The processing means are preferably configured to determine geometric and/or optical characteristics of the eye lens based on the cross-sectional images and the wavefront profile. The processing means are, in particular, configured to determine the topography and/or the refractive power of the lens on the basis of the cross-sectional images and the wavefront profile. The processing means are, for example configured to determine wave aberration of the eye on the basis of the wavefront profile, to determine the cornea topography of the eye based on the cross-sectional images, and to determine the refractive power of the lens on the basis of the wave aberration and the cornea topography.

In one embodiment variant, the measurement apparatus has further image detection means for detection of a view image of the eye, which view image has an image of the cross-sectional part that is illuminated by the first light projector and/or the mirror image of the pattern on the eye, and in order to store this view image associated with the cross-sectional image. Furthermore, the measurement apparatus has processing means for positioning of the stored cross-sectional image relative to the eye on the basis of the associated stored view image. The detection and storage of the cross-sectional image and of the view image associated with it with the illuminated cross-sectional part allows the determination of the position of the cross-sectional image or of the illuminated cross-sectional part detected in it relative to the eye on the basis of the associated view image of the cross-sectional part illuminated by the first light projector and/or of the mirror image of the pattern on the eye.

BRIEF DESCRIPTION OF THE DRAWING

One embodiment of the present invention will be described in the following text with reference to one example. The example of the embodiment is illustrated by the following attached figures.

APPROACHES TO IMPLEMENTATION OF THE INVENTION

In FIGS. 1, 5, 6, 7, 8, 9, 10, the reference symbol 1 denotes an opthalmological measurement apparatus, with various embodiments of the opthalmological measurement apparatus 1 being explained in the following description, with reference to these figures. Otherwise, mutually corresponding identical components in the figures are annotated with the same reference symbols.

Figure 1:
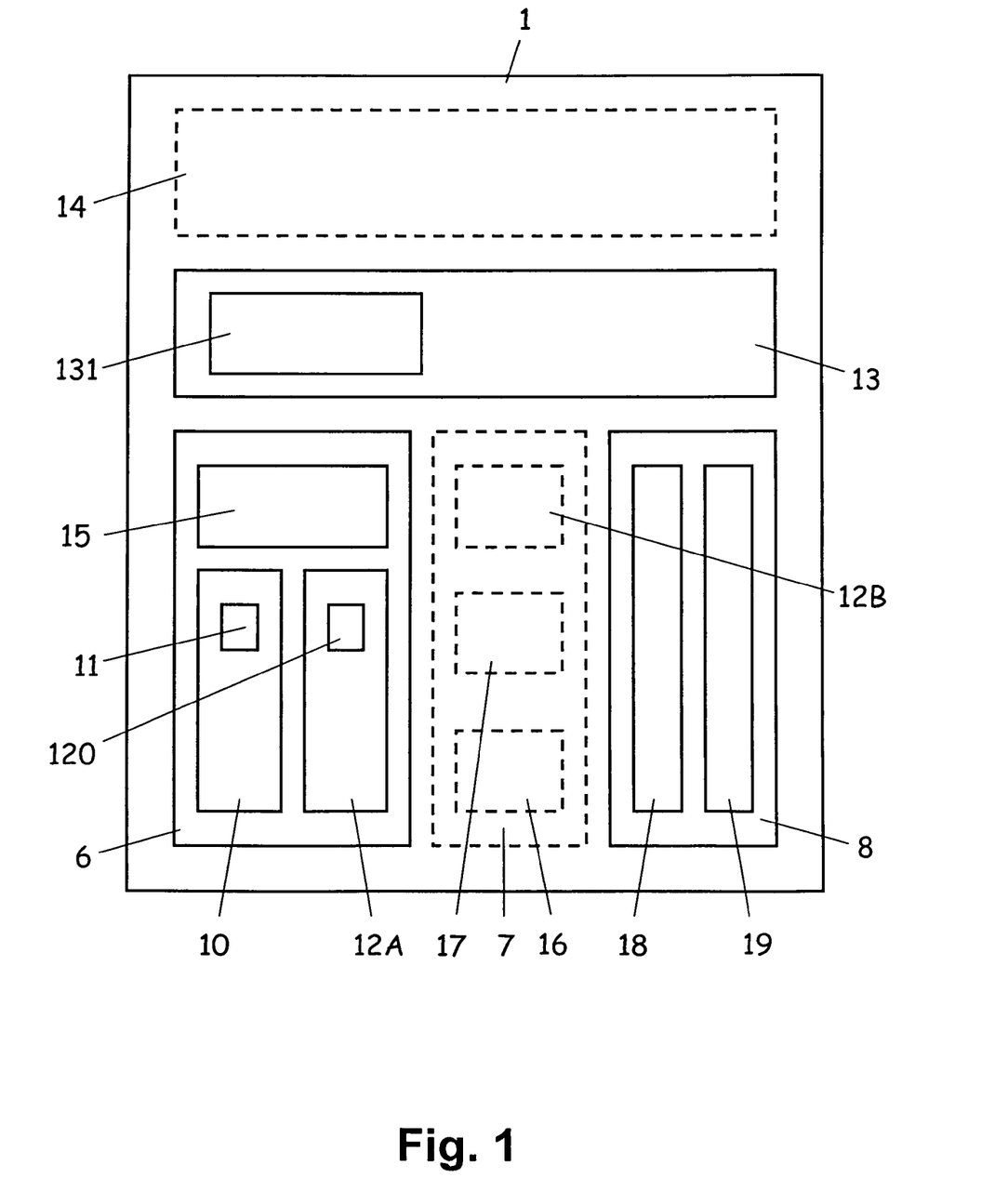
FIG. 1 shows a block diagram which schematically illustrates an opthalmological measurement apparatus which has a plurality of different measurement systems, a display as well as processing means with a control module.

As is illustrated in FIG. 1, the opthalmological measurement apparatus 1 has a first measurement system 6 with a first light projection system 10 an image detection means 12A, a second measurement system 8 with a second light projection system 18 and a wavefront detector 19, as well as an optional third measurement system 7 with image detection means 12B, an additional light source 16 and a shielding body 17. The image detection means 12B are preferably used for detection of view images from the first and third measurement systems 6, 7, jointly. The first light projection system 10 has a light projector 11. The image detection means 12A has an image converter 120. The opthalmological measurement apparatus 1 also has control elements, which are not illustrated, an optional display 14 on which specific measurement values and/or application aids are displayed, as well as processing means 13, with a control module 131 and further functional modules for processing of measurement data which is recorded by the measurement systems 6, 7, 8. The processing means 13 have at least one processor, data and program memory. The functional modules are preferably in the form of programmed software modules, which are stored in the program memory and are run on the processor. Those skilled in the art will understand that the functional module may also be provided entirely or partially in the form of hardware. The electrical feed for the opthalmological measurement apparatus 1 is provided by means of an internal energy source, or by means of an external energy source connected by means of a cable or cables.

At this point, it should be stated that one embodiment variant of the opthalmological measurement apparatus 1 is configured only to detect the measurement data which is detected by the measurement systems 6, 7, 8 and has an appliance interface for transmission of this measurement data to functional modules which are arranged externally to the opthalmological measurement apparatus 1.

Figure 2:
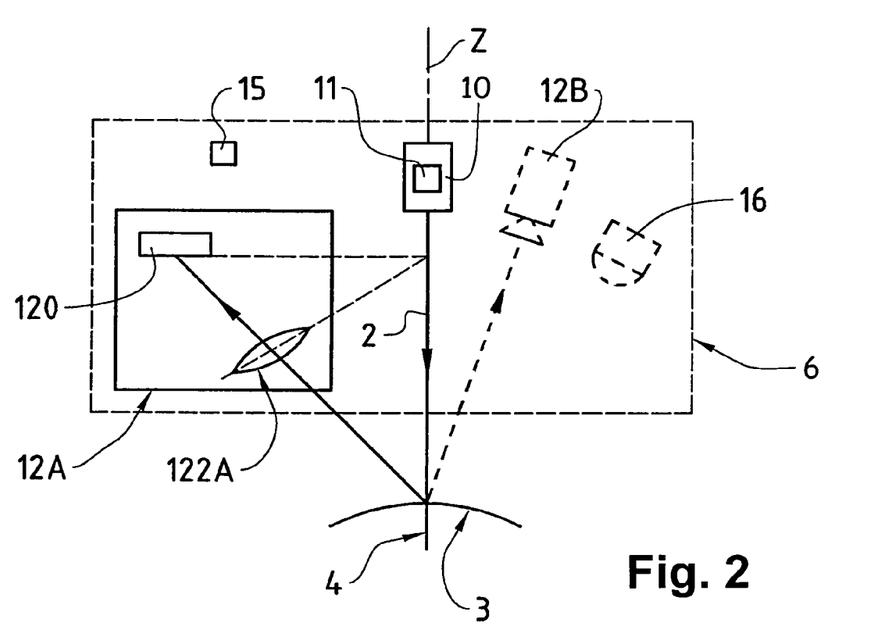
FIG. 2 shows a block diagram which schematically illustrates a first measurement system for the opthalmological measurement apparatus, which has a first light projection system, an image detection apparatus for detection of a cross-sectional image of an eye, and an optional image detection apparatus for detection of a view image of the eye.
Figure 3:
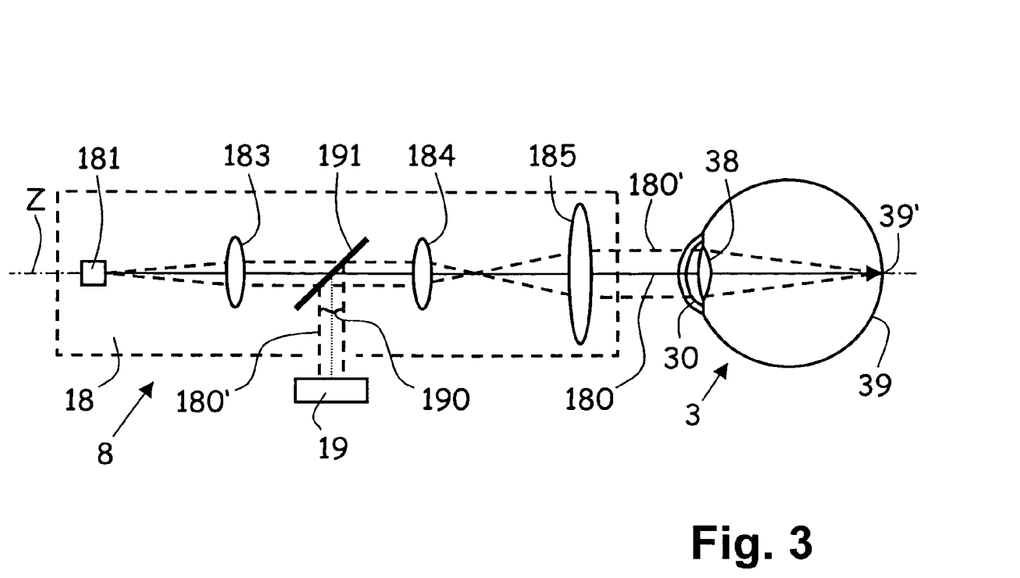
FIG. 3 shows a block diagram which schematically illustrates a second measurement system for the opthalmological measurement apparatus, which has a second light projection system as well as a wavefront detector.
Figure 4:
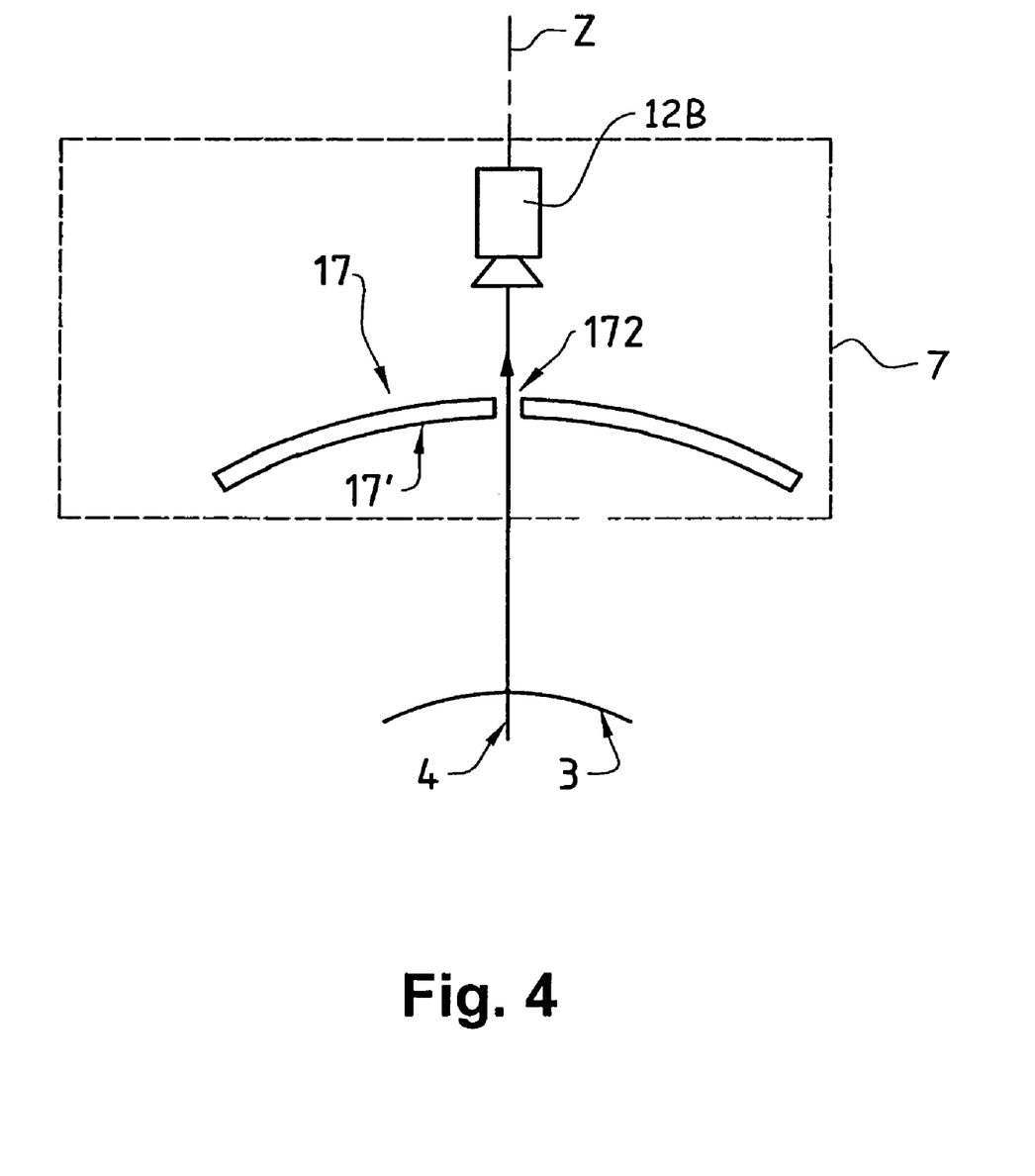
FIG. 4 shows a block diagram which schematically illustrates a third measurement system for the opthalmological apparatus, which has an image detection apparatus for detection of a view image of the eye, as well as a perforated shielding body.

One embodiment of the first measurement system 6 is illustrated in detail in FIG. 2. FIG. 3 shows a detailed illustration of one embodiment of the second measurement system 8, and FIG. 4 shows a detailed illustration of the third measurement system 7.

As is illustrated schematically in FIGS. 2, 5, 6, 7, 8, 9, 10, the (first) light projection system 10 or the light projector 11 is configured to project a beam 2 through a cross-sectional part 4 of the eye 3, in particular through a cross-sectional part 4 of the cornea 30 of the eye 3. The beam 2 is preferably projected in the form of a light slit. The light projection system 10 or the light projector 11 has, for example, a slit lamp or a laser, whose light in formed into a fan by beam-forming optics.

As is illustrated in FIGS. 2, 5, 6, 7, 8, 9, 10, the first measurement system 6 or the opthalmological measurement apparatus 1 also has image detection means for detection and storage of a cross-sectional image 30A of at least one subregion of the cross-sectional part 4 illuminated by the light projector 11, which are arranged in the Scheimpflug configuration with respect to the beam 2.

The embodiments of the first measurement system 6 or of the opthalmological measurement apparatus 1 illustrated in FIGS. 2, 5, 6, 7, 8, 9, 10 also have further image detection means for detection of a view image 3A of the eye 3, which comprises an image of the illuminated cross-sectional part 4A, and for storage of the detected view image 3A and of the image of the illuminated cross-sectional part 4A contained therein, associated with the detected cross-sectional image 30A.

As is illustrated in FIGS. 2, 5, 7, 8, 9, 10, depending on the embodiment of the first measurement system 6 or of the opthalmological measurement apparatus 1, the image detection means has image detection apparatuses 12A, 12B, for example CCD cameras (Charged Coupled Device) or CMOS cameras (Complementary Metal-Oxide Silicon), image converters 120, for example CCD chips of CMOS chips, beam-deflecting elements 121A, 121B, for example mirrors, and/or imaging optical elements 122A, 122B, for example optical lenses.

For visualization of natural eye features, such as the limbus 33, iris 34 or pupil 35, and/or for projection of synthetic light marks 36, the embodiments of the first measurement system 6 or of the opthalmological measurement apparatus 1 illustrated in FIGS. 2, 5, 6, 7, 8, 9, 10 have one or more additional light sources 16. For example, one or more infrared light-emitting diodes may be used in particular for visualization of natural eye features. The natural and/or synthetic reference features are also included in the view image 3A of the eye 3.

Although, for simplicity, this is not illustrated in the figures, the opthalmological measurement apparatus 1 has a fixing target in order to fix the eye 3 in the accommodated state and/or unaccommodated state (fixed alignment and refractive power of the eye 3). The fixing target is, for example, an image which is projected to the patient by means of a further light beam into the eye 3.

As is illustrated schematically in FIG. 3, the (second) light projection system 18 or the light projector 181 for the second measurement system 8 is configured for projection of a beam 180 through the cornea 30 and the eye lens 38 to the retina 39 of the eye 3. The beam 180 is preferably in the form of a fine beam, and projects a spot 39, which is approximately in the form of a point, onto the retina 39, for example by means of the imaging optical elements 183, 184, 185, for example optical lenses. By way of example, the beam 180 is a parallel beam. In order to focus the beam 180 onto the retina 39, the light projection system 18 furthermore has, for example a conventional optical zoom system, which is not illustrated, or a lens arrangement. The beam 180' which is scattered back diffusely from the retina 39 passes back through the eye lens 38 and the cornea 30 to the light projection system 18, where it is supplied to the wavefront detector 19, in order to determine the wavefront profile 190, for example through the imaging optical elements 185, 184, for example optical lenses, and the beam-deflecting optical element 191, for example a semi-reflective mirror. In the embodiment variants according to 5, 7, 9, the light beam 180' that is scattered back diffusely is supplied to the wavefront detector 19 via a plurality of beam-deflecting optical elements 182, 191. The beam deflecting elements (lenses) are omitted in FIGS. 5, 6, 7, 8, 9, 10, for simplicity. By way of example, the wavefront detector 19 is in the form of a Shack-Hartmann sensor, for example, according to US 2003/0038921, or an interferometer, for example a Shearing interferometer. Further possible embodiments of the wavefront detector 19 are described in Jos. J. Rozena, Dirk E. M. Van Dyck, Marie-José Tassignon, "Clinical comparison of 6 aberrometers. Part 1: Technical specifications", J Cataract Refract Surg, Volume 31, June 2005, pages 1114-1127.

Figure 5:
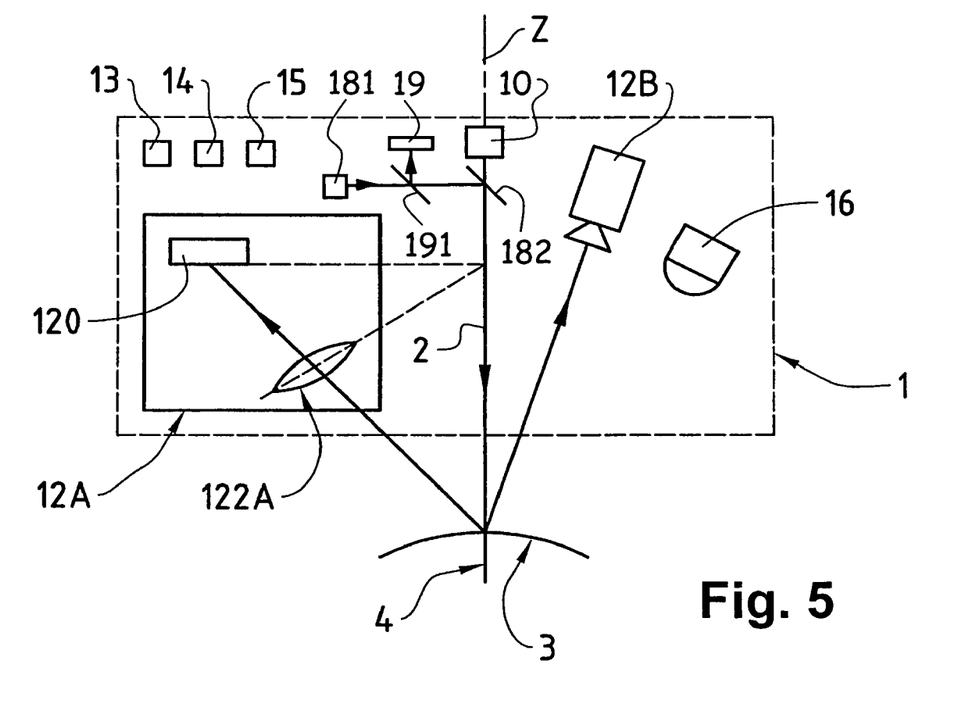
FIG. 5 shows a block diagram which schematically illustrates an opthalmological measurement apparatus which has a first and a second measurement system.
Figure 6:
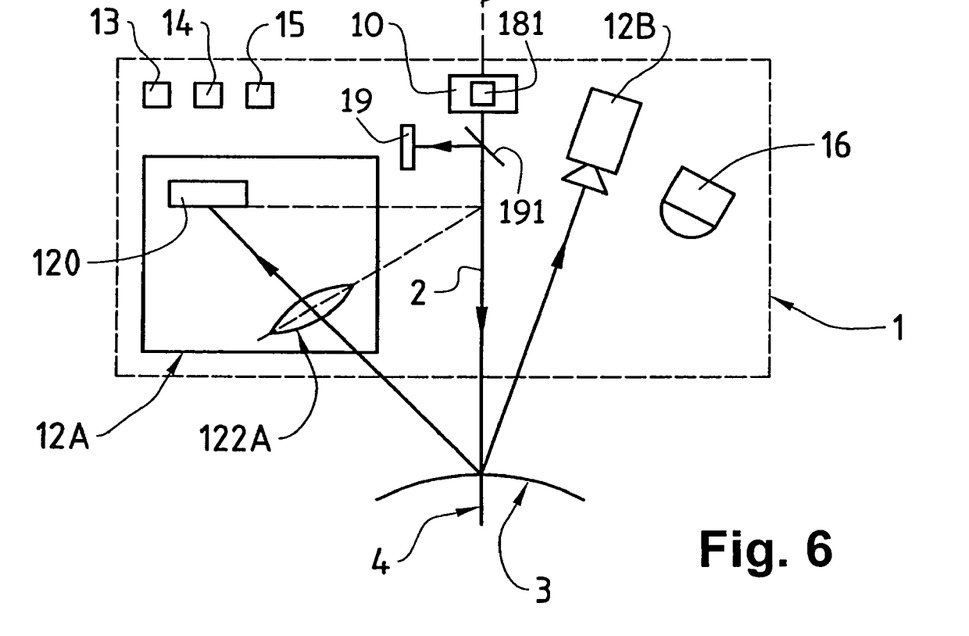
FIG. 6 shows a block diagram which schematically illustrates an opthalmological measurement apparatus which has a first and second measurement system with the light projector for the second measurement system being part of the light projection system for the first measurement system.
Figure 10:
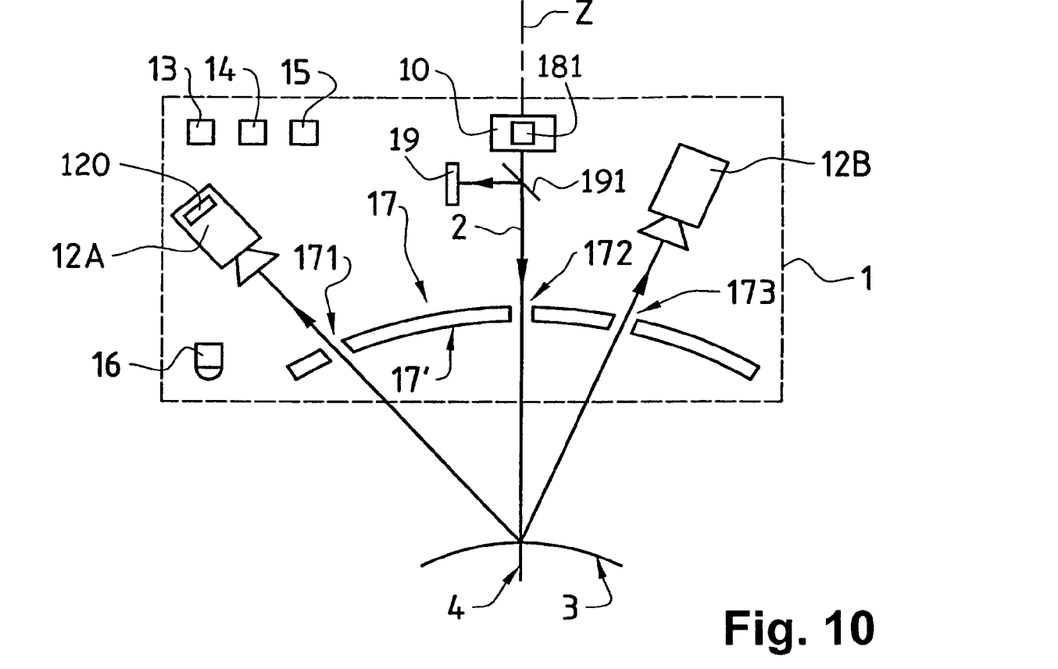
FIG. 10 shows a block diagram which schematically illustrates an opthalmological measurement apparatus which has a first, a second and a third measurement system, with the light projector for the second measurement system being part of the light projection system for the first measurement system.

As is illustrated in FIGS. 5, 6, 7, 8, 9, 10, the light projection systems 10, 18 or the light projectors 11, 181 are preferably arranged such that the beams 2, 180 are projected along a common radiation axis Z onto the eye 3, preferably along the sagittal axis of the eye 3, which is defined by fovea and the center of the pupil 35 (and possibly by the fixing target) or by the visual (or optical) axis of the eye 3. As is illustrated in FIGS. 5, 7, 8, 9, the opthalmological measurement apparatus 1 has, in various embodiment variants, a beam-deflecting optical element 182, for example a semi-reflective mirror, for introduction of the beam 180 onto the radiation axis Z. In alternative embodiment variants, the light projector 181 as is illustrated in FIGS. 6 and 10 is arranged in the light projection system 10. This means that the light beam 180 which is emitted from the light projector 181 for the second measurement system 8 is projected via optical elements, for example imaging and/or beam-deflecting optical elements, in the light projection system 10 of the first measurement system 6 along the radiation axis Z onto the eye 3.

Figure 7:
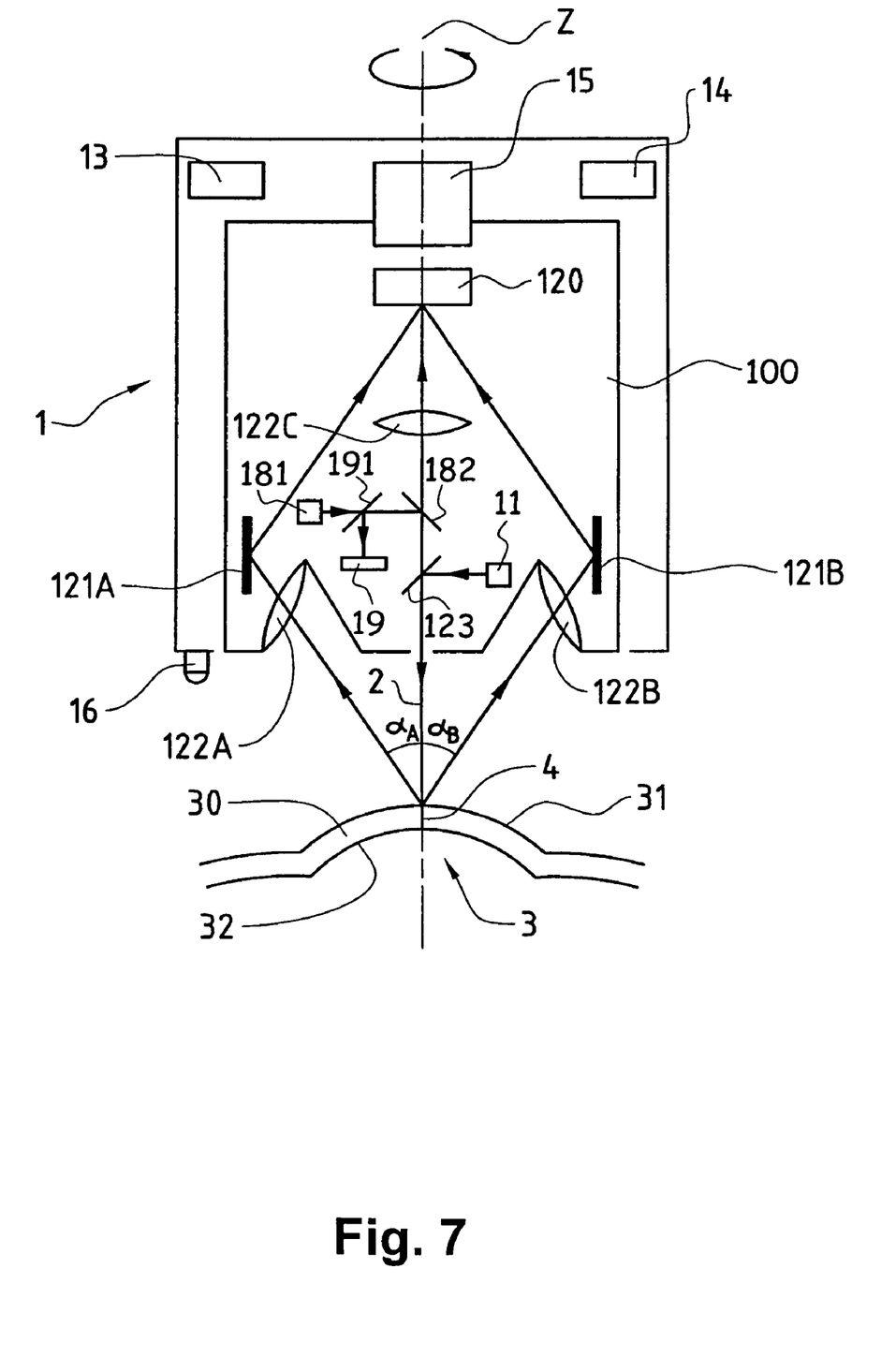
FIG. 7 shows a block diagram which schematically illustrates an opthalmological measurement apparatus which has a first and a second measurement system, with the first measurement system having a light projector and image detection means for detection of two cross-sectional images and of a view image of an eye.
Figure 8:
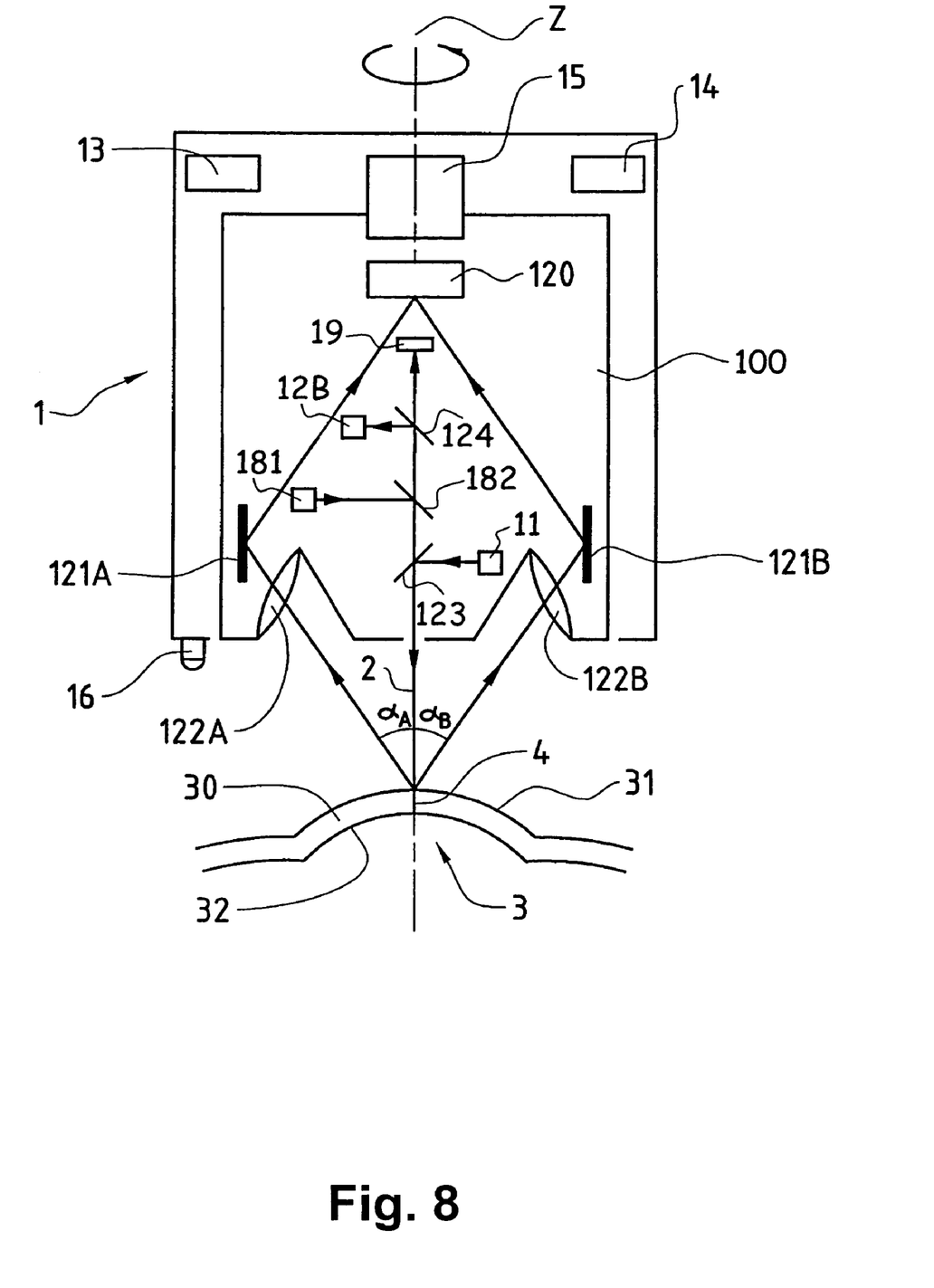
FIG. 8 shows a block diagram which schematically illustrates an opthalmological measurement apparatus which has a first and a second measurement system, with the first measurement system having a light projector and image detection means for detection of two cross-sectional images and of a view image of an eye, and with the wavefront detector for the second measurement system being part of an image converter for the first measurement system.
Figure 9:
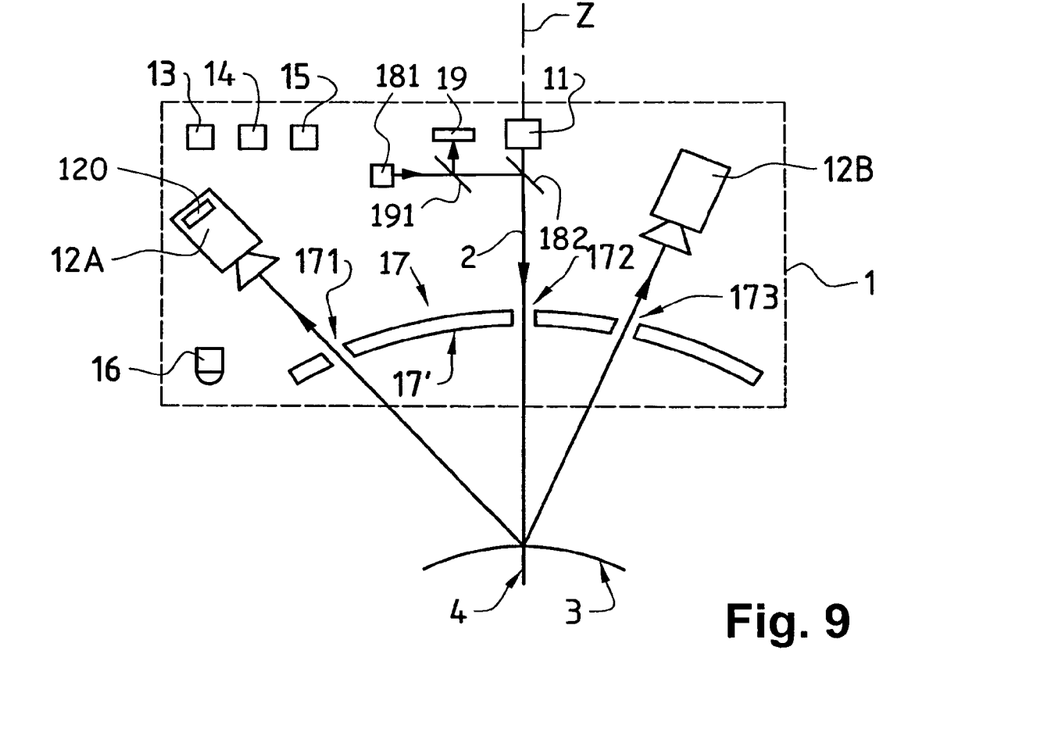
FIG. 9 shows a block diagram which schematically illustrates an opthalmological measurement apparatus which has a first, a second and a third measurement system.

In the embodiment variants shown in FIGS. 7, 8, the beam 2 which is emitted from the light projector 11 is passed via a beam-deflecting optical element 123, for example a semi-reflective mirror, onto the radiation axis Z. In one embodiment variant, the light projectors 11, 181 are fed from a common light source, for example a laser. The light projectors 11, 181 preferably, however, have their own light sources, each at different wavelengths. In one embodiment variant, the light projector 11 has a light source for production of light in the blue range (blue-light source), and the light projector 181 has a light source for production of light in the infrared range (infrared light source).

In the embodiments shown in FIGS. 5, 6, 7, 8, the opthalmological measurement apparatus 1 has a combination of the first measurement system 6 and of the second measurement system 8. In the embodiments shown in FIGS. 9, 10, the opthalmological measurement apparatus 1 has a combination of the first measurement system 6, of the second measurement system 8 and of the third measurement system 7.

In the embodiments shown in FIGS. 5 and 6, the image detection means 12A for detection and storage of cross-sectional images 30A have imaging optical elements 122A and an image converter 120, which is arranged in the Scheimpflug configuration with the projected beam 2.

Figure 12A:
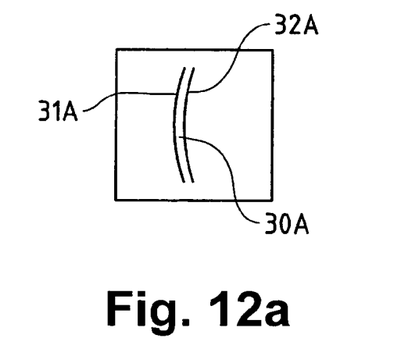
FIG. 12a shows a cross-sectional image of an illuminated cross-sectional part of an eye (cornea).
Figure 12B:
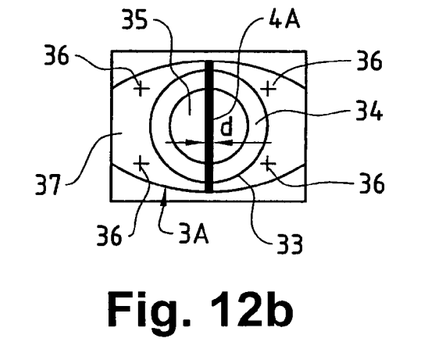
FIG. 12b shows a view image on an eye with an illuminated cross-sectional part.

FIG. 12a shows a cross-sectional image 30A, detected by the image detection apparatus 12A, of the illuminated cross-sectional part 4 of the eye 3. In particular, a cross-sectional image of the front cornea surface 31A and a cross-sectional image of the rear cornea surface 32A can be seen in the cross-sectional image 30A. Although this is not shown, the cross-sectional image 30A also includes a cross-sectional image of the front lens surface and a cross-sectional image of the rear lens surface. The optical axis of the separate image detection apparatus 12B for detection of the view image 3A of the eye 3 is located outside the beam 2. The view image 3A of the eye 3 illustrated in FIG. 12b in fact corresponds to a view image which is detected as a plan view by an image detection apparatus 12B, with the image detection apparatus 12B being arranged such that its optical axis runs essentially parallel to the optical axis of the eye 3, or, preferably, coincides with the radiation axis Z. In particular, an image of the illuminated cross-sectional part 4A with the finite thickness d, the projected light marks 36 as well as the limbus 33, iris 34 and pupil 35 of the eye can be seen in the view image 3A. Light marks, are, for example, highlights of light-emitting diodes or projected points. Projection locations are, for example, the sclera 37 or the cornea 30.

Figure 13:
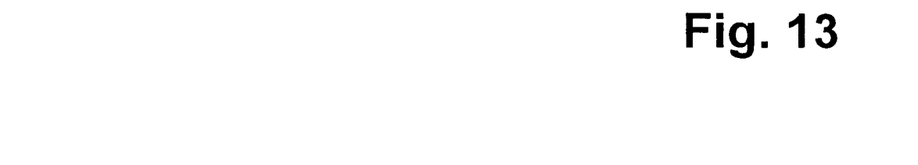
FIG. 13 shows a combined image with a cross-sectional image of an illuminated cross-sectional part of an eye, and with a view image of the eye with the illuminated cross-sectional part.

In the embodiments shown in FIGS. 7 and 8, the opthalmological measurement apparatus 1 has a preferred arrangement in which the radiation axis Z and the optical axis of the image detection means for detection of the view image 3A coincide. The image detection means have a common image converter 120 for detection of two cross-sectional images 30A, 30B composed on two different positions and, as shown in FIG. 7, for detection of the view image 3A as well. The imaging optical elements 122A and the beam-deflecting optical element 121A emit the light beams for detection of the cross-sectional image 30A from a first position at the observation angle $\alpha_A$ for detection to the image converter 120. The additional imaging optical elements 122B and the additional beam-deflecting optical element 121B pass the light beams for detection of the cross-sectional image 30B from a second position at the observation angle $\alpha_B$ for detection, likewise to the image converter 120. The two positions are preferably located on different sides of the beam 2, and the observation angles $\alpha_A$ and $\alpha_B$ are preferably of the same magnitude. As shown in FIG. 8, the light beams for detection of the view image 3A are passed via a (wavelength-selective) beam-deflecting optical element 124 to the image detection apparatus 12B. FIG. 13 shows one possible combination of a cross-sectional image 30A, a view image 3A and a cross-sectional image 30B, which is detected by the image converter 120 in the embodiments shown in FIG. 7. The functional modules of the processing means 13 have programmed evaluation modules which determine eye structures in the detected and stored cross-sectional images 30A, 30B, in particular images of the cornea with the front cornea surface 31A, 31B and the rear cornea surface 32A, 32B as well as images of the lens with the front lens surface and the rear lens surface. By way of example, distances or thicknesses are determined on this basis, in particular the measurement values $D_A$ and $D_B$ of the distances between the front cornea surface 31A, 31B and the rear cornea surface 32A, 32B, in order to determine the cornea thickness.

Figure 11:
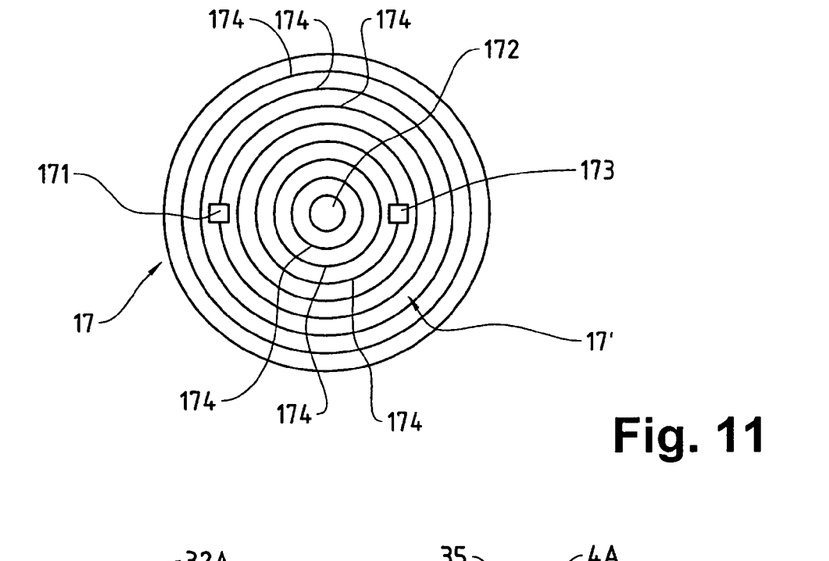
FIG. 11 shows a view of the side of a shielding body facing the eye, with perforations and with a visible pattern.

As is illustrated in FIGS. 1, 2, 5, 6, 7, 8, 9, 10, the first measurement system 6 or the opthalmological measurement apparatus 1 has a drive module 15 for rotation of the light projection system 10 or of the light projector 11 and the image detection means 12A, essentially about a normal with respect to the surface of the eye 3 facing the light projector 11, or for linear movement of these components essentially at right angles to this normal. As is illustrated schematically in FIGS. 7 and 8, the light projection system 10, with the light projector 11 and the beam-deflecting optical element 123, as well as the image detection means, with the image converter 120, the beam-deflecting optical elements 121A, 121B and the imaging optical elements 122A, 122B, are for this purpose fitted to a moving mount apparatus 100, which is driven by the drive module 15. The components on the second and third measurement systems 7, 8 and of the mount apparatus 100 are preferably also fitted. The drive module 15 preferably has a rotation driver, for example an electric motor, which rotates the mount apparatus 100 around the radiation axis Z. The entire eye 3 is measured by rotation of the light projector 11 and of the image detection means around the radiation axis Z. In the embodiments shown in FIGS. 9 and 10, the opthalmological measurement apparatus 1 has a perforated shielding body 17. The perforations 171, 172, 173 in the shielding body 17 are in each case arranged such that the beam paths to the image detecting means 12A, 12B and to the light projector 11 can pass through the shielding body 17 without any impediment. A visible pattern 17', a so-called placido pattern, for example with circular rings 174, is applied to the side of the shielding body 17 facing the eye 3, and is reflected by the surface of the eye 3. Light sources can also be fitted on or adjacent to the shielding body 17, facing the eye 3, for example light projectors 16 for projection of light marks 36. FIG. 11 illustrates a view of the side of the shielding body 17 facing the eye 3, with perforations 171, 172, 173 and with the visible pattern 17'. The reflection of the visible pattern 17' on the eye surface is imaged by the image detection means 12B in the view image 3A, and can be used for the positioning of the cross-sectional images 30A as a synthetic reference pattern for the determination of the relative position of the opthalmological measurement apparatus 1 with respect to the eye 3. The shielding body 17 is preferably connected to the drive module 15 such that it is also moved with the light projector 11 and the image detection means. In one alternative embodiment, the shielding body 17 can also be fitted to the opthalmological measurement apparatus 1 such that it is not coupled to the drive module 15, with the perforations 171, 172, 173 being appropriately adapted. At this point, it should be stated that the shielding body 17 can also be combined with the embodiments shown in FIGS. 7 and 8. Furthermore, the shielding body 17 can also be arranged such that the image detection means 12A, 12B and/or the light projector 11 are located between the shielding body 17 and the eye 3, in this case with the image detection means 12A, 12B and/or the light projector 11 being fitted, for example, on the side of the shielding body 17 facing the eye 3.

The coupling of the second measurement system 8 to the drive module 15 allows the wavefront detector 19 to be moved to different positions with respect to the eye 3, for example rotationally essentially about a normal to the surface of the eye 3 (for example the sagittal axis) and/or translationally essentially at right angles to this normal, so that the wavefront profile 190 of the light beam 180' which is scattered back diffusely from the eye 3 (in particular from the retina 39) can be detected from a plurality of positions, and can be stored. Sine the wavefront detector 19 typically has an arrangement with a limited number of individual lenses, for example an array of 32×32 lenses, the detection and storage of wavefront profiles from a plurality of positions makes it possible to increase the resolution of the wavefront detector 19, and thus of the second measurement system 8. This improved resolution of the wavefront profile is achieved independently of the first and third measurement systems 6, 7 by means of an opthalmological measurement apparatus for determination of a wavefront profile which has a measurement system 8 with a light projection system 18 for projection of a light beam 180 onto the eye 3, and with a wavefront detector 19 for determination and storage of a wavefront profile 190 of the light beam 180' reflected by the eye 3, as well a drive module 15, with the drive module 15 and the wavefront detector 19 being arranged and coupled such that the wavefront detector 19 is moved to different positions with respect to the eye 3. The opthalmological measurement apparatus for determination of the wavefront profile is also configured to detect and to store the wavefront profile 190 from these different positions. In addition, the opthalmological measurement apparatus for determination of the wavefront profile has a data memory for storage of the wavefront profiles detected from different positions, in each case associated with position details relating to this, for example in the form of an angle or in the form of coordinates. The opthalmological measurement apparatus for determination of the wavefront profile furthermore preferably has specifically configured processing means 13 for determination of an overall wave profile with improved resolution from the stored wavefront profiles 190, for example by (weighted) averaging.

The control module 131 is configured to control the function and the operation of the opthalmological measurement apparatus 1. In particular, the control module 131 is configured to selectively activate the first, second and/or third measurement system 6, 8, 7, the drive module 15 and/or the light projectors 16, in order to detect and to store one or more cross-sectional images 30A and respectively associated view images 3A, the wavefront profile 190 and/or one or more mirror images of the pattern 17' from one or more positions with or without projected light marks 36. The control module 131 is configured to receive selected operating modes or commands via control elements from the user, to determine a functional procedure associated with the selected operating mode or command, to control the first, second and/or third measurement system 6, 7, 8 as well as the drive module 15 in accordance with the defined functional procedure, and to determine one or more eye characteristics based on the detected cross-sectional images 30A, view images 3A, wavefront profile 190 and/or mirror images on the basis of the chosen operating mode or command, or the associated functional procedure. In principle, the cross-sectional images 30A, view images 3A and mirror images can be detected at the same time. Simultaneous detection of the wavefront profile is possible when light sources at different wavelengths are used for the light projectors 11, 181, and when wavelength-selective beam-deflecting optical elements 191, 182 are used. The measurement systems are activated with time delays for detection of associated measurement data at the same wavelengths from the light projectors 11, 181, for example in a defined sequence corresponding to the user-selected operating mode or command. In a further embodiment variant of light projectors 11, 181 at the same wavelength, the scattered light from the front eye section (lens, iris) is masked out by the use of a conjugate image, for example by means of a perforated shutter.

The functional modules of the processing means 13 have a programmed positioning module which determines the position of a stored cross-sectional image 30A relative to the eye 3. The relative positioning is carried out on the basis of the view images 3A, which are respectively associated with the cross-sectional images 30A. The position of the cross-sectional image 30A is determined by determining the position of the eye 3 relative to the opthalmological measurement apparatus 1. In this case, the relative position of the opthalmological measurement apparatus 1 with respect to the eye 3 is determined on the basis of the image of the illuminated cross-sectional part 4A, the natural features of the eye 3, the imaged synthetic reference features, for example the imaged light marks 36, and/or the detected mirror image of the pattern 17'.

The functional modules of the processing means 13 also have a programmed composition module, which positions a plurality of detected and stored cross-sectional images 30A relative to one another. With knowledge of the geometric arrangement of the opthalmological measurement apparatus 1, the composition module joins the detected and stored cross-sectional images 30A corresponding to their relative position with respect to the eye 3 or with respect to one another to form a three-dimensional image of the eye 3, in particular to form a three-dimensional (cross-section-base) cornea topography of the eye 3.

A further functional module, the programmed surface determination module, determines an approximate (pattern-based) cornea topography of the eye 3 on the basis of the detected mirror image of the pattern 17'. The pattern-based cornea topography is used by the composition module to complete the cross-section-based cornea topography when, for example individual cross-sectional images 30A are partially or completely missing because of eyelash movement or other shadowing. In one embodiment variant, a combined cornea topography is determined by weighted averaging from the pattern-based cornea topography in the cross-section-based cornea topography, for example as a function of the measurement uncertainty of the two measurement methods.

Further functional features are configured to determine geometric and/or optical characteristics of the eye lens 38, in particular its topography and refractive power, on the basis of the cross-sectional images 30A and the wavefront profile 190. The programmed optics module first of all determines the wave aberration of the eye 3 on the basis of the detected wavefront profile 190. The programmed lens determination module determines the refractive power of the eye lens 38 on the basis of the wave aberration and of the cornea topography of the eye 3. The previously determined cross-section-based and/or pattern-based cornea topography of the eye 3 can be used as the basis for determination of the refractive power. The lens determination module determines the geometry of the eye lens 38 on the basis of the refractive power of the eye lens 38, of the cornea topography of the eye 3 and of the cross-sectional images 30A, 30B. In particular, the lens determination module defines the rear lens surface and the front lens surface of the eye lens 38 on the basis of the refractive power of the eye lens 38, of the cornea topography of the eye 3 and of the cross-sectional images 30A, 30B. The lens determination module preferably uses ray-tracing methods for this purpose. The lens determination module uses the cornea topography to follow the light beams as far as the front lens surface. The lens determination module follows this further back to the rear lens surface, with the aid of the refractive power of the lens.

Finally, a further functional module, the equalization module, supplies, as a further end result in addition to the geometric eye model (cornea topography, lens topography), equalized cross-sectional images for display on the display 14. In particular, the equalization module uses the geometry of the eye lens determined by the lens determination module to produce better-quality, that is to say equalized, cross-sectional images of the eye lens.

The invention claimed is:

1. An opthalmological measurement apparatus, comprising:
   a first measurement system, the first measurement system comprising:
     a first light projection system for projection of a first light beam through a cross-sectional part of an eye, and
     image detection means for detection and storage of a cross-sectional image of at least one subregion of the cross-sectional part which is illuminated by the first light projection system, from a first position outside the first light beam, which are arranged in a Scheimpflug configuration with respect to the first light beam;
   a second measurement system, the second measurement system comprising:
     a second light projection system for projection of a second light beam onto the eye, and
     a wavefront detector for determination and storage of a wavefront profile of the second light beam reflected by the eye; and
   processing means configured to determine at least one eye characteristic based on both the wavefront profile and the cross-sectional image.

2. The measurement apparatus of claim 1, wherein the processing means are configured to determine one or more geometric and/or optical characteristics of the eye based on the wavefront profile and one or more cross-sectional images detected and stored by the image detection means.

3. The measurement apparatus of claim 1, wherein the processing means are configured to determine geometric and/or optical characteristics of the lens of the eye based on the wavefront profile and a plurality of cross-sectional images detected and stored by the image detection means.

4. The measurement apparatus of claim 1, wherein the processing means are configured to determine the refractive power of the lens based on the wavefront profile and a plurality of cross-sectional images detected and stored by the image detection means.

5. The measurement apparatus of claim 1, wherein the processing means are configured to determine wave aberration of the eye based on the wavefront profile, to determine cornea topography of the eye based on a plurality of cross-sectional images detected and stored by the image detection means, and to determine the refractive power of the lens based on the wave aberration and the cornea topography.

6. The measurement apparatus of claim 1, comprising a control module configured to activate the measurement systems, in accordance with a user-selected operating mode, in a defined sequence successively for detection of the wavefront profile and one or more cross-sectional images, and wherein the processing means are configured to determine the at least one eye characteristic, corresponding to the user-selected operating mode, based on the wavefront profile and the one or more cross-sectional images.

7. The measurement apparatus of claim 1, wherein the first light projection system and the second light projection system are arranged such that the first light beam and the second light beam are projected along a common radiation axis onto the eye.

8. The measurement apparatus of claim 1, wherein the first measurement system is configured to project the first light beam through a plurality of differently positioned cross-sectional parts of the eye, and to detect in the Scheimpflug configuration and to store a plurality of cross-sectional images of in each case at least one subregion of these illuminated cross-sectional parts.

9. The measurement apparatus of claim 1, comprising a drive module for rotation of the first measurement system essentially about a normal to the surface of the eye facing the first light projection system, or for linear movement of the first measurement system essentially at right angles to this normal.

10. The measurement apparatus of claim 1, wherein the first measurement system and the second measurement system are configured for simultaneous detection of the cross-sectional image and the wavefront profile.

11. The measurement apparatus of claim 1, wherein the first light projection system is configured to project the first light beam in the form of a light slit.

12. The measurement apparatus of claim 1, wherein the first light projection system and the second light projection system have a common light source.

13. The measurement apparatus of claim 1, wherein the wavefront detector is in the form of a Shack-Hartmann Sensor.

14. The measurement apparatus of claim 1, wherein the measurement apparatus further comprises a third measurement system, the third measurement system comprising a shielding body with a visible pattern with the shielding body being arranged such that the visible pattern is located, during application of the measurement apparatus, on a side of the shielding body facing the eye, and image detection means configured to detect and store a mirror image of the pattern on the eye; and the processing means are configured to determine a pattern-based cornea topography of the eye based on the mirror image, to determine a cross-section-based cornea topography of the eye based on a plurality of cross-sectional images, and to determine a combined cornea topography of the eye based on the pattern-based cornea topography and the cross-section-based cornea topography.

15. The measurement apparatus of claim 14, wherein the shielding body is configured and arranged such that the first light beam can be projected without any impediment through the cross-sectional part of the eye, such that the cross-sectional image can be detected without any impediment, such that the second light beam can be projected without any impediment onto the eye and such that the second light beam reflected by the eye can be detected without any impediment.

16. The measurement apparatus of claim 1, comprising further image detection means for detection of a view image of the eye, which view image comprises at least one of an image of the cross-sectional part that is illuminated by the first light projection system and a mirror image of a pattern on the eye, and for storing this view image associated with the cross-sectional image, and wherein the processing means are configured to position the stored cross-sectional image relative to the eye based on the associated stored view image.

* * * * *